United States Patent [19]

Allgood

[11] Patent Number: 5,122,122
[45] Date of Patent: Jun. 16, 1992

[54] LOCKING TROCAR SLEEVE

[75] Inventor: Fred A. Allgood, Fort Worth, Tex.

[73] Assignee: Dexide, Incorporated, Fort Worth, Tex.

[21] Appl. No.: 440,199

[22] Filed: Nov. 22, 1989

[51] Int. Cl.$^5$ ............................................. A61B 17/34
[52] U.S. Cl. .................... 604/174; 604/167; 604/169; 604/105
[58] Field of Search ............ 604/164, 167, 169, 107, 604/174, 105; 606/198

[56] References Cited

U.S. PATENT DOCUMENTS

| | | | |
|---|---|---|---|
| 3,039,468 | 6/1962 | Price | 604/164 X |
| 3,713,447 | 1/1973 | Adair | 604/169 X |
| 3,946,741 | 3/1976 | Adair | 604/164 X |
| 4,240,411 | 12/1980 | Kosono | 604/167 X |
| 4,393,873 | 7/1983 | Nawash et al. | 604/174 X |
| 4,601,710 | 7/1986 | Moll | 604/165 |
| 4,627,838 | 12/1986 | Cross et al. | 604/164 X |
| 4,655,752 | 4/1987 | Honkanen et al. | 604/167 X |
| 4,861,334 | 8/1989 | Nawaz | 604/164 X |
| 4,909,798 | 3/1990 | Fleischhacker et al. | 604/167 X |
| 4,931,042 | 6/1990 | Holmes et al. | 604/164 |

FOREIGN PATENT DOCUMENTS

| | | | |
|---|---|---|---|
| 3042229 | 5/1982 | Fed. Rep. of Germany | 604/167 |
| 1344166 | 1/1974 | United Kingdom | 604/167 |

*Primary Examiner*—Michael H. Thaler
*Attorney, Agent, or Firm*—Jackson & Walker

[57] ABSTRACT

An improved trocar sleeve (10) is disclosed for use in laparoscopic surgery. The sleeve (10) is provided with an expanded mushroom hinge (20) at the first end (14) of the sleeve inserted into the abdominal cavity. The mushroom hinge (20) can be expanded within the abdominal cavity to abut against the inner surface of the abdominal wall (18) to hold the sleeve in place. A split seal (52) having a concave shape facing the first end (14) of the trocar sleeve (10) is provided to prevent loss of pressurized gas from within the abdominal cavity through the sleeve (10) as the pressure of the gas itself urges the first and second seal lips (78, 80) on opposite sides of the slit in the seal into sealing engagement.

2 Claims, 3 Drawing Sheets

LOCKING TROCAR SLEEVE

TECHNICAL FIELD

The present invention relates in general to medical devices and more particularly relates to an improved trocar sleeve which can be inserted a short distance into the abdominal cavity and expanded to prevent the sleeve from sliding in and out of the incision.

BACKGROUND OF THE INVENTION

In the past few years, laparoscopic surgery has become increasingly important and widespread. In the past, when doing surgery within the abdominal cavity, a large incision through the abdominal wall was required to permit the surgeon to adequate view the area to be operated on. The development of the laparoscope, a small telescope utilizing fiber optic technology, allows the surgeon to view a cite to be operated on within the abdominal cavity with an incision only large enough to insert the laparoscope. With such a small incision required, laparoscopic surgery reduces the risk of infection to the patient and the extent of trauma to the body during the surgery. The surgery also reduces the chance of adhesions resulting from exposure of the interior of the body, a relative common occurrence in prior surgery.

In conducting laparoscopic surgery, a small incision is typically cut through the abdominal wall for insertion of a cannula. Pressurized carbon dioxide gas passes through the cannula to inflate the abdomen to create voids for passage of the laparoscope. After inflation, the cannula is removed.

A trocar, or sharp pointed instrument, is then used to form an incision through the abdominal wall which will be used for insertion of the laparoscope. A trocar sleeve is concentric with the trocar, with only the sharp end of the trocar exposed from the trocar sleeve. Thus, when the trocar is inserted through the abdomen wall, a first end of the trocar sleeve is pushed through the abdomen wall into the abdominal cavity. The trocar is withdrawn from both the abdomen and trocar sleeve, leaving the first end of the trocar sleeve within the abdominal cavity. The laparoscope, or other suitable apparatus, can then be inserted through the interior of the trocar sleeve into the abdominal cavity. One example of a trocar assembly is disclosed in U.S. Pat. No. 4,601,710 issued Jul. 22, 1986.

While such techniques have proven useful, several disadvantages remain. The trocar sleeve has a tendency to slide in and out of the incision in the abdominal wall, particularly when the surgeon is trying to move the laparoscopic instrumentation through the interior of the trocar sleeve into or out of the abdominal cavity. Further, seals are provided in the passage through the trocar sleeve to prevent the carbon dioxide gas from escaping the abdominal cavity. It is often difficult and time consuming to force the laparoscopic instrumentation or other device past these seals into the abdominal cavity. Therefore, a need exists for an improved apparatus and method for performing such laparoscopic surgery.

SUMMARY OF THE INVENTION

An improved trocar assembly is provided for use in inserting a laparoscopic instrument into the abdominal cavity. The trocar assembly includes a trocar sleeve having a first end extending into the abdominal cavity through an incision in the abdominal wall. The first end has a first external diameter for passage through the incision. The trocar assembly further has structure for expanding a portion of the first end within the abdominal cavity so that the external dimension of the first end within the abdominal cavity is a larger, second external diameter. The expanded first end of the trocar sleeve abuts the inner abdominal wall about the incision to resist withdrawal of the trocar sleeve from the abdominal cavity.

In accordance with another aspect of the present invention, the trocar sleeve includes a first sleeve portion and a second sleeve portion, the sleeve portions being concentric. The first sleeve portion has a mushroom hinge thereon at the first end of the trocar sleeve. The structure for expanding the portion of the first end causes the first and second sleeve portions to move relative one another along their longitudinal axes to expand the mushroom hinge. The structure can include a spring for moving the sleeve portions relative one another and a latch mechanism for holding the spring in a compressed state with the first end of the trocar sleeve having the first external dimension. Release of the latch mechanism allows the spring to expand, causing the sleeve portions to move and expand the mushroom hinge.

In accordance with another aspect of the present invention, a trocar sleeve is provided which has a first end extending into the abdominal cavity through an incision in the abdominal wall. The trocar sleeve has a passage formed therethrough which extends from the abdominal cavity to the exterior, A seal is mounted in the trocar sleeve along the passage. The seal is formed of a resilient material and has a concave shape facing the first end of the trocar assembly within the abdominal cavity. A slit is formed in the seal, forming first and second seal lips on opposite sides of the slit. In the absence of a laparoscopic instrument, the pressure within the abdominal cavity urges the first and second lips together to form a seal at the slit. When a laparoscopic instrument is inserted through the passage, the first and second lips are resiliently deflected to permit passage of the instrument.

In accordance with another aspect of the present invention, a method for inserting a trocar sleeve through the abdominal wall for laparoscopic surgery is provided. The method includes the step of forming an incision through the abdominal cavity with a trocar and passing a first end of a trocar sleeve into the abdominal cavity. The first end of the trocar sleeve having a first external dimension for passage through the incision. The method further includes the step of expanding a portion of the first end within the abdominal cavity so that the external diameter of the first end within the cavity is expanded to a larger, second external dimension to abut the inner surface of the abdominal wall about the incision to resist withdrawal of the trocar sleeve from the abdominal cavity.

BRIEF DESCRIPTION OF THE DRAWINGS

Further features and advantages of the invention will become more apparent from the following Detailed Description and illustrated in the accompanying drawings, in which.

DETAILED DESCRIPTION

Figure 1:
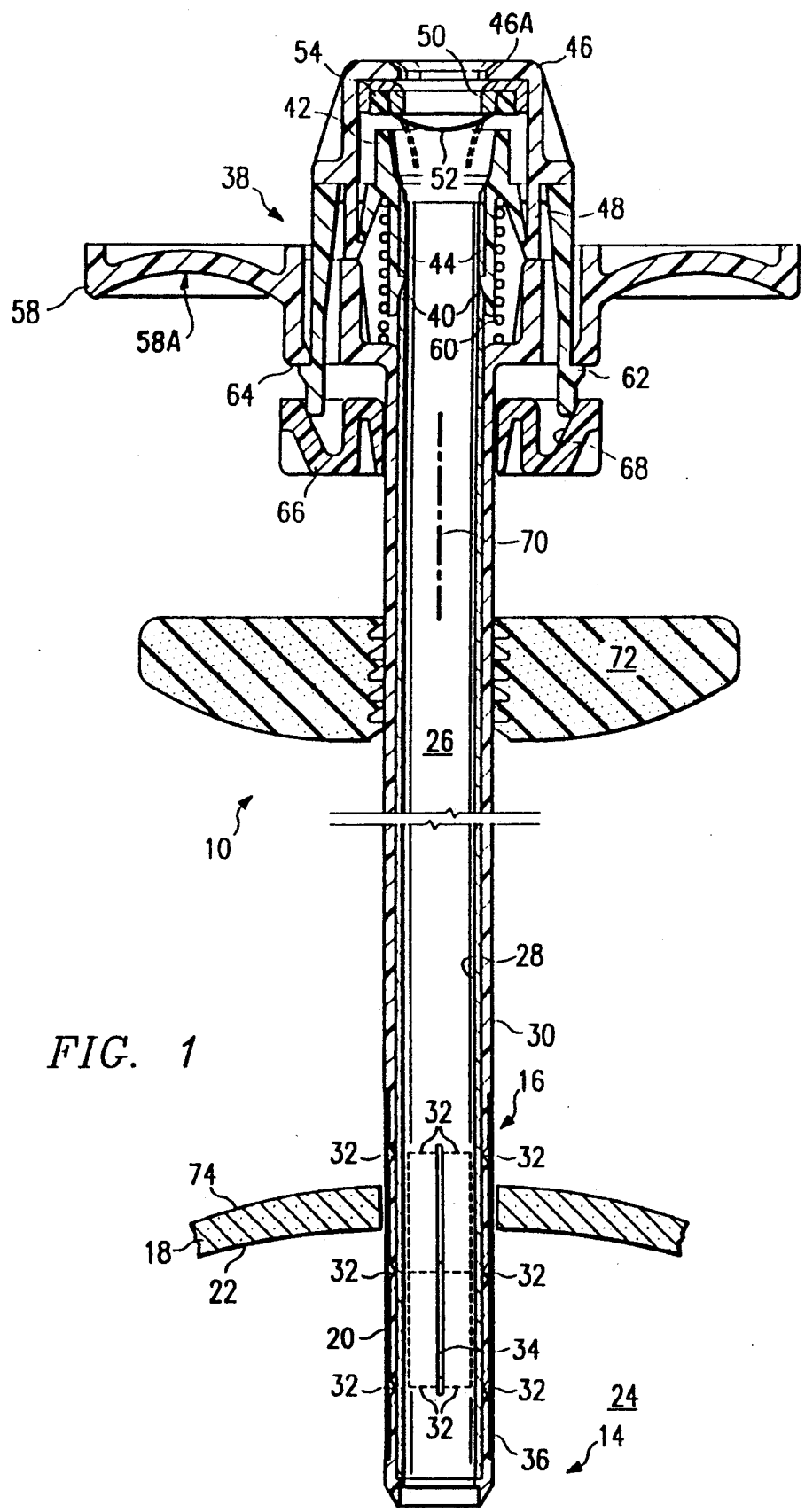
FIG. 1 is a side view of a trocar sleeve forming a first embodiment of the present invention prior to expansion.
Figure 2:
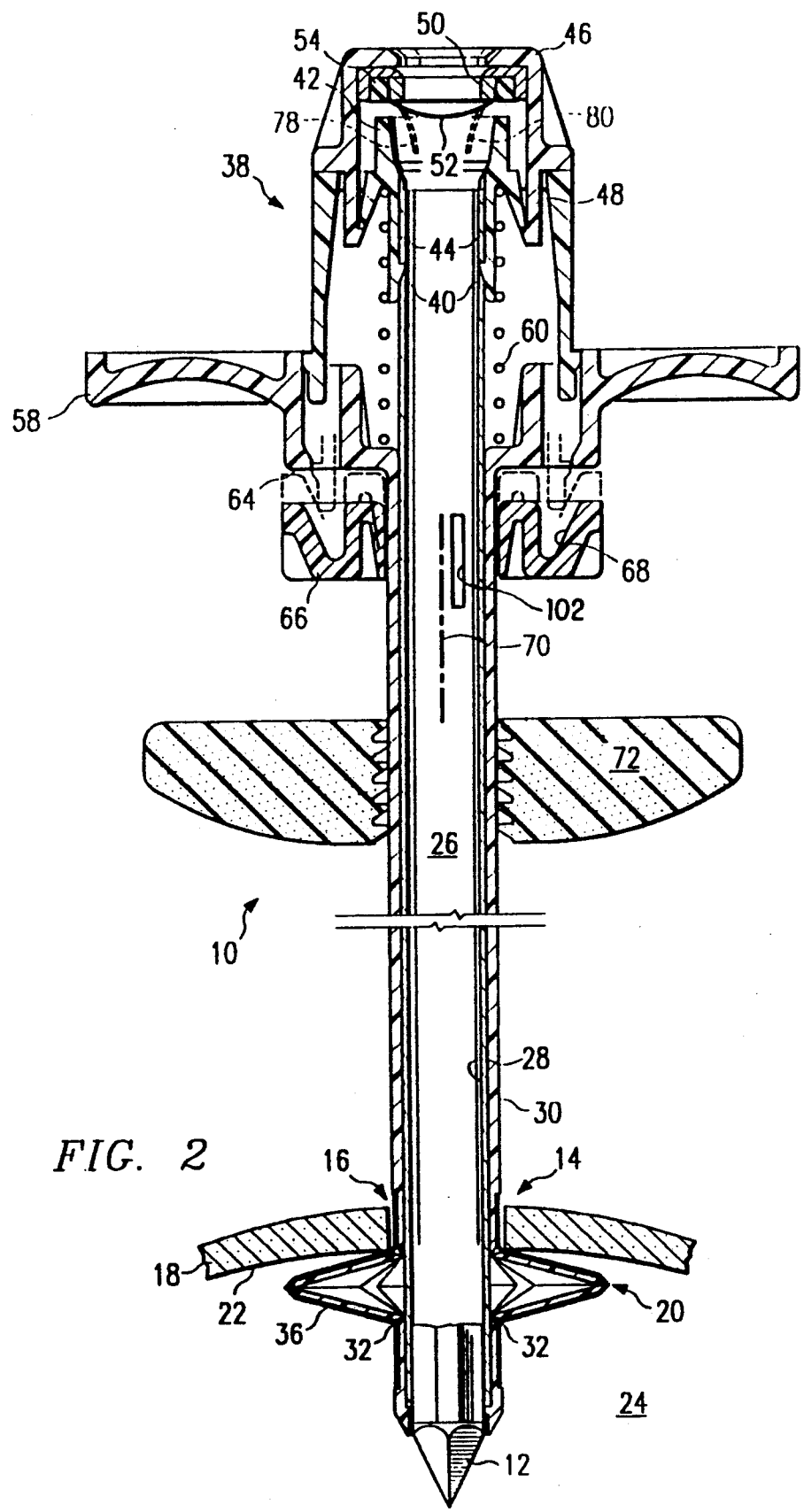
FIG. 2 is a side view of the trocar sleeve after expansion of the mushroom hinge.
Figure 3:
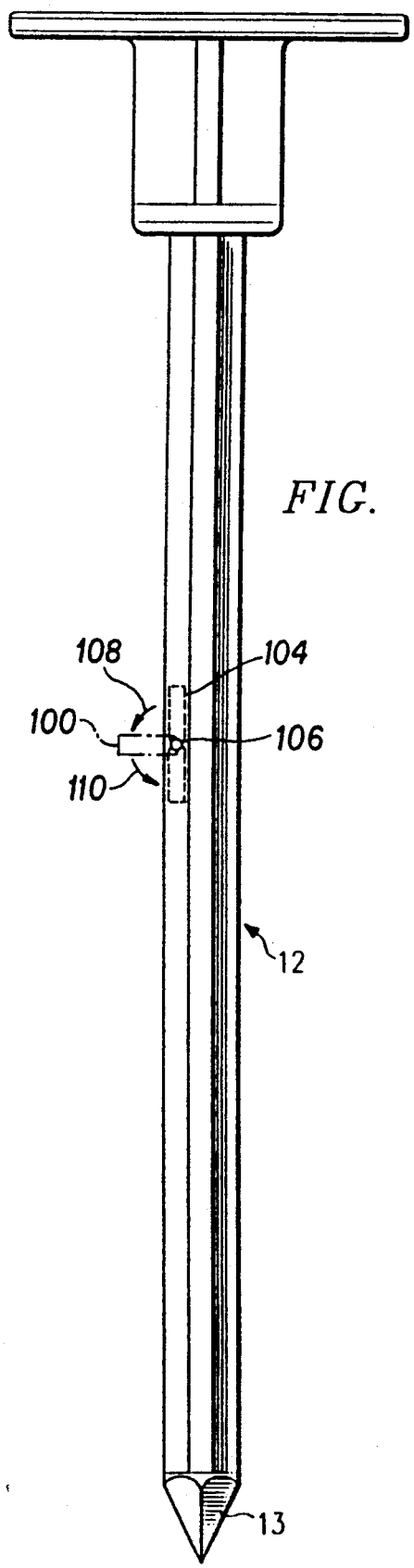
FIG. 3 is a side view of a trocar used with the trocar sleeve.

With reference now to FIGS. 1-3, a trocar sleeve 10 forming a first embodiment of the present invention is illustrated. With the assistance of a trocar 12, seen in FIG. 3, a first end 14 of the sleeve 10 is inserted through an incision 16 in the abdominal wall 18 of a patient. The trocar 12 is inserted through passage 26 in the trocar sleeve so that only the sharp pointed end 13 extends from the first end 14 of sleeve 10. The pointed end of trocar 12 then is pushed through the abdominal wall along with first end 14. The sleeve 10 is secured therein by expansion of a mushroom hinge 20 which abuts the inside surface 22 of the abdominal wall about the incision 16 to prevent premature withdrawal of the trocar sleeve. After removal of trocar 12, laparoscopic instruments and the like can be inserted into the abdominal cavity 24 through passage 26 in the trocar sleeve 10.

With reference to FIGS. 1 and 2, the trocar sleeve 10 can be seen to include an inner cylindrical metal sleeve 28 and a concentric outer cylindrical plastic sleeve 30 preferably of polypropylene. The sleeves 28 and 30 are bonded or fastened together at the first end 14. Near the first end 14, the outer plastic sleeve 30 defines mushroom hinge 20 with a series of living hinges 32 about the circumference of the sleeve 30 separated by elongated slits 34. An outer elastic coating or sleeve 36, preferably of latex, overlies the living hinges 32 and slits 34 to cover the mushroom hinge 20. Coating or sleeve 36 insures that no body tissue is trapped between portions of the mushroom hinge, particularly when contracting the hinge for removal of the sleeve 10 from the patient.

At end 38 of the trocar sleeve opposite the first end, the metal sleeve 28 has a series of openings 40. A plastic end member 42 is secured to the metal sleeve 28 at end 38 by latches 44 received in the openings 40.

A plastic seal retaining cap 46 is, in turn, secured to the end member 42 by latches 48 on the cap. An O.D. seal 50, a split seal 52, and a pack ring 54 are confined between the end member 42 and cap 46 to prevent the pressurized gas within the abdominal cavity from escaping through the passage 26 in the metal sleeve 28 as will be described hereinafter. Seals 50 and 52 are preferably of silicon rubber.

A handle 58 is secured to the outer plastic sleeve 30 at end 38. A coil spring 60 acts between the end member 42 and the handle 58 to urge the handle 58 toward the first end of the trocar sleeve.

In the configuration illustrated in FIG. 1, the coil spring 60 is held in a compressed state between the end member 42 and the handle 58 as resilient latches 62 on the end member 42 are in contact with an end surface 64 of the handle.

A latch release 66 is received about the outer plastic sleeve 30 for movement relative the sleeve 30. The latch release 66 can be seen to have a conical camming surface 68 which can be moved into engagement with the ends of latches 62 to deflect the latches inward toward the axis 70 of the trocar sleeve 10. The latch release 66 can be activated by the surgeon directly, or, as an alternative, by providing a mechanism whereby withdrawal of the trocar after inserting the sleeve through incision 16 activates the latch release. The latches 62 will be deflected inward enough to release the handle 58 from the end member 42, which permits the spring 60 to expand to the position shown in FIG. 2. As the spring expands, the spring forces the handle 58, and attached outer plastic sleeve 30, toward the first end relative to the end member 42 and inner metal sleeve 28. This causes the portions of the plastic sleeve 30 at the living hinges to bend and expand the mushroom hinge 20, as seen in FIG. 2. It can be readily understood that the expanded mushroom hinge abuts the inside surface 22 of the abdominal wall 18 to resist removal of the trocar sleeve.

A dense rubber foam stop 72 can be frictionally engaged with the outer plastic sleeve 30. When the mushroom hinge has been expanded, the stop 72 can be slid downward along the plastic sleeve 30 toward the first end to contact the outer surface 74 of the abdominal wall 18 to resist movement of the trocar sleeve into the abdominal cavity.

It can be readily understood that the trocar sleeve 10 provides a stable platform for insertion of a laparoscopic instrument or the like through the sleeve 10 into the abdominal cavity through passage 56. The expanded mushroom hinge 20 also forms a good seal with the patient's abdominal wall 18 to prevent $CO_2$ loss. Any tendency for the trocar sleeve 10 to move relative the abdominal wall as the instrument is being inserted or removed will be greatly reduced by the expanded mushroom hinge 20 and stop 72.

Figure 4:
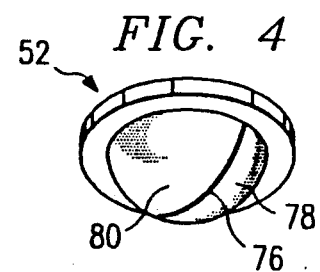
FIG. 4 is a perspective view of a seal within the trocar sleeve.

When the trocar sleeve 10 is to be removed from the patient, surface 46A is pressed towards the handle 58 at surface 58A in a manner similar to a syringe to collapse the mushroom hinge 20 and compress the spring 60 until the latches 62 again latch against surface 64 of the handle 58 to allow removal of the trocar sleeve. The mushroom hinge 20 can be collapsed and removed without having to move stop 72.

with reference now to FIGS. 1, 2 and 4, the mechanism for preventing gas from escaping the abdomen through the sleeve 10 will be described. When no laparoscopic instrument is inserted through the trocar sleeve 10, a split seal 52 prevents the escape of gas. The split seal 52 is formed of a resilient material which has a concave curvature facing the first end 14 of the trocar sleeve. A slit 76 is formed in the split seal which forms a first seal lip 78 and a second seal lip 80 on opposite sides of the slit 76. With the concave shape, the pressurized gas within the abdominal cavity acts to force the lips 78 and 80 together to form a tight seal to prevent the gas escape. When an instrument in inserted in end 38 of the trocar sleeve 10, the resilient lips 78 and 80 simply deflect away from the instrument, permitting the instrument to pass through the passage and into the abdominal cavity.

The O.D. seal 50 forms a seal against the outer cylindrical surface of an instrument as the instrument is inserted into the passage 26 of trocar sleeve 10. With the combination of the O.D. seal 50 and split seal 52, very little gas is lost as instruments are inserted and removed from the trocar sleeve 10.

Figure 5:
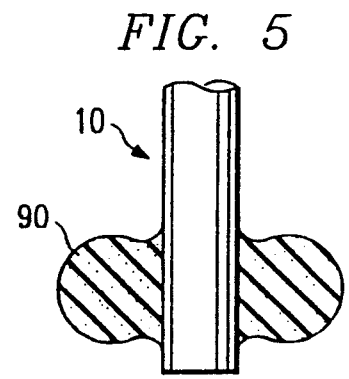
FIG. 5 is an illustrative view of a first modification of the trocar sleeve where an expanding sponge is used.

With reference to FIG. 5, a first modification of the trocar sleeve 10 is illustrated. In the first modification, an expanding sponge 90 replaced the mushroom hinge 20 at the first end of the trocar sleeve 10. The sponge 90 can be expanded in a manner similar to the mushroom hinge 20 to hold the trocar sleeve within the abdominal cavity.

Figure 6:
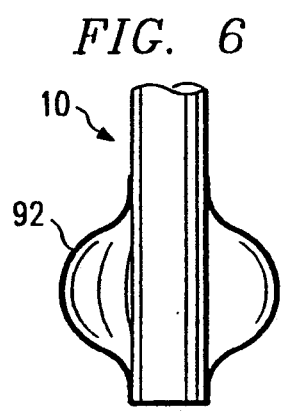
FIG. 6 is an illustrative view of a second modification of the trocar sleeve where an inflatable balloon is used.

With reference to FIG. 6, a second modification of trocar sleeve 10 is illustrated. In the second modification, an inflatable balloon 92 is mounted at the first end of the trocar sleeve which can be inflated to an expanded condition to secure the trocar sleeve within the abdominal cavity.

The sleeve 10 of the present invention reduces the frictional forces encountered by laparoscopic instruments being inserted into or removed from the sleeve as compared to prior designs. One reason for this advantage is that the entire sleeve 10 can be made shorter than past designs which required a longer length to insert through the abdominal wall to resist accidental removal of the sleeve from the patient. Another reason for the friction reduction is the use of efficient seals 50 and 52.

The trocar 12 can be used to automatically expand mushroom hinge 20 as the trocar is removed from sleeve 10. One possible mechanism for this is illustrated in FIGS. 2 and 3. A lever 100 can be pivoted to trocar 12 about hinge 106 and urged outwardly by a spring 104, The lever will be retracted into the trocar 12 as the trocar is inserted into the sleeve 10 to place the sleeve 10 through incision 16. When the trocar is removed from sleeve 10, the lever extends outward in the direction of arrow 108 through a slot 102 in the sleeve so that the lever 100 contacts latch release 66. Further movement of trocar 12 would cause the release 66 to move upward and deploy the mushroom hinge. The lever 100 can be mounted to retract back into trocar 12 in the direction of arrow 110 after sufficient force has been exerted on trocar 12 to move release 66 to allow the trocar to be removed from sleeve 10.

In one possible construction of a sleeve in accordance with the teachings of the present invention, the inner diameter of the sleeve could be about 5 to 6 mm. with the diameter of the expanded hinge about 0.845 inches. The stroke of the sleeve 30 to activate the hinge could be ⅜ inches and sleeve 36 could be 10 mils thick.

While the preferred embodiment of the present invention has been described in detail and shown in the accompanying drawings, it will be evident that various further modifications and uses not illustrated are possible without departing from the scope of the invention.

I claim:
1. An improved trocar assembly for use in inserting a laparoscopic into the abdominal cavity, comprising:
   a trocar sleeve defining a passageway and having a first and second end, said first end having a first external dimension adapted for passage through an incision in an abdominal wall, and a second end for manipulation of the trocar sleeve;
   means for expanding a portion of the first end of said trocar sleeve when placed within the abdominal cavity so that the external dimension of the first end may be expanded to a second external dimension to resist withdrawal of the trocar sleeve from the abdominal cavity;
   a stop slidably disposed over the second end of said trocar sleeve which can be adjusted to contact the skin of the patient;
   a split seal mounted to said trocar sleeve within the passageway, said split seal being formed of resilient material having a concave curvature facing the first end of the trocar sleeve, a slit being formed in the split seal to define first and second seal lips facing each other such that gas pressure in the abdominal cavity urges the first and second seal lips into sealing engagement but which will permit deflection and passage of a laparoscopic instrument through the trocar sleeve
   said trocar sleeve including a first sleeve portion and a second sleeve portion, the sleeve portions being concentric relative to each other, said first sleeve portion having a mushroom hinge thereon, said means for expanding a portion of the first end causing the first and second sleeve portions to move relative to each other to expand the mushroom hinge, said means for expanding a portion of the first end including a spring acting between said first and second sleeve portions to expand the mushroom hinge.

2. The improved trocar assembly of claim 1 wherein a handle is mounted on the first sleeve portion and an end member is mounted on said second sleeve portion, the spring acting between said handle and end member, said handle and end member having cooperating latch structure to compress the spring and hold the mushroom hinge in a contracted position for insertion and removal from the incision.

* * * * *